United States Patent [19]

Parkhurst et al.

[11] Patent Number: 4,562,298

[45] Date of Patent: Dec. 31, 1985

[54] OPTICALLY ACTIVE NORDIHYDROGUAIARETIC ACID AND INTERMEDIATES

[75] Inventors: Robert M. Parkhurst, Redwood City, Calif.; Ronald S. Pardini, Reno, Nev.

[73] Assignee: Chemex Pharmaceuticals, Inc., Denver, Colo.

[21] Appl. No.: 436,444

[22] Filed: Oct. 25, 1982

[51] Int. Cl.[4] .................. C07C 43/205; C07C 43/263; C07C 39/16

[52] U.S. Cl. .................................... 568/644; 568/636; 568/646; 568/729; 556/482

[58] Field of Search . 566/482; 568/636, 646, 644, 729

[56] References Cited

U.S. PATENT DOCUMENTS

| | | | |
|---|---|---|---|
| 2,456,443 | 12/1948 | Mueller et al. | 568/729 X |
| 2,644,822 | 7/1953 | Pearl | 568/644 X |
| 3,769,350 | 10/1973 | Perry | 568/644 X |
| 3,843,728 | 10/1974 | Perry | 568/331 |
| 3,906,004 | 9/1975 | Perry | 568/644 X |

OTHER PUBLICATIONS

Biftu et al., Jour. Chem. Soc., Perkin I, (1979), 2276-2281.
Perry et al., Jour Org. Chem., 37:26, (1972), 4371-4376.
Schrecker et al., J.A.C.S., 77, (1955), 432-437.
Gisvold et al., J. Amer. Pharm. Assoc., 35 (1946), 188-191.

*Primary Examiner*—Bernard Helfin
*Attorney, Agent, or Firm*—Sheridan, Ross & McIntosh

[57] ABSTRACT

A process for producing novel compositions including optically active molecules of nordihydroguaiaretic acid (d,1-2,3-dimethyl,1,4-bis(3,4-dihydroxyphenyl)butane) and intermediates, starting with 1,4-bis(3,4-dimethoxyphenyl)butanone, or other structurally similar composition having oxy substituents at the 3,4-phenyl positions, comprising (1) forming the corresponding butanol; (20) forming the corresponding 1,4-butane ether or siloxy composition; (3) cleaving the oxy substituent from the butane chain at the 1 and 4 positions; (4) dealkylating the phenols at the 3,4 positions to leave hydroxy substituents with hydrobromic acid reflux for 8 to 10 hours. Optical orientation is preserved throughout.

3 Claims, No Drawings

OPTICALLY ACTIVE NORDIHYDROGUAIARETIC ACID AND INTERMEDIATES

TECHNICAL FIELD

This invention pertains to organic compounds and their syntheses, in particular to d,1-nordihydroguaiaretic acid, and optically active intermediates.

BACKGROUND ART

In the past, meso-nordihydroguaiaretic acid, (N.D.G.A.), expensively derived from *Larrea divaricata* or *Larrea tridentata*, the creosote bush, or snythesized from phenyl ethers, has been used as a food additive and anti-oxidant. Optically active N.D.G.A. and racemic mixtures thereof are also useful for this purpose. The d,1-form, as distinguished from the meso-form, gives a pleasant odor to soaps and toilet articles; and is more soluble than its meso isomer. The optically active N.D.G.A. (and racemic mixture thereof) of this invention is distinguished from the meso form by its melting point of 157° C. to 160° C., as opposed to the 185° C. to 186° C. melting point of the meso form. Racemic 2,3-dimethyl,1,4-bis(3,4-dimethoxyphenyl)-1,4-butanedione has served as an intermediary in the synthesis of meso-N.D.G.A. in prior art processes, but the optical orientation of the 2,3-dimethyl bonds has been lost in subsequent processing steps. This invention involves the preservation of the optical orientation of these bonds through reduction, methylation and cleavage steps to produce optically active molecules, or a racemic mixture of N.D.G.A., as well as the diols and ethers intermediate to the synthesis. Insofar as the optically active isomers and racemic mixture of N.D.G.A. may be utilized in place of the meso form thereof, the synthesis of d,1-N.D.G.A. provided herein fulfills the need for an easier, less expensive method of production, providing product in higher yields than prior art processes, without the use of high pressure hydrogenation equipment and expensive catalysts.

PRIOR ART STATEMENT

U.S. Pat. No. 2,456,443 to Mueller, et al., provides a synthesis of an N.D.G.A. of melting point 185°–186° C. (the melting point of the meso form) by bromination of safrole (3,4-methylenedioxy-alkylbenzene), coupling the resultant molecules to form 2,3-bis(3,4-methylenedioxybenzyl)-butane, chlorinating this compound to form 2,3-bis(3,4-dichloromethylenedioxybenzyl)-butane, and hydrolyzing this compound to form N.D.G.A. The intermediates of the present process are not involved.

U.S. Pat. No. 2,644,822 to Pearl discloses processes for reacting benzaldehydes having a hydroxy group or a potential hydroxy (oxy) group at the 4-position (para to the aldehyde group) and at least another hydroxy or potential hydroxy group at the 3-position to produce ketone and diol intermediaries, and a final nordihydroxybutanediol product. Where the examples provide melting points for this product, they are given as 185°–186.5° C., corresponding with the meso form of the product. In each case, the diols are formed from ketones by means of bimolecular reduction reactions. The process of the present invention does not utilize bimolecular reduction, but rather the reduction of a diketone.

C. W. Perry, M. V. Kalnins and K. H. Deitcher, "Synthesis of Lignans, I. Nordihydroguaiaretic Acid," *J. Org. Chem.* 37, 4371 (1972) discloses the synthesis of meso-N.D.G.A. by alkylation of the sodium enolate of propioveratrone (3,4-dimethoxypropiophenone) with α-bromopropioveratone (α-bromo-3,4-dimethoxypropiophenone) to form racemic 2,3-dimethyl,1,4-bis (3,4-dimethoxyphenyl)1,4-butanedione. Cyclodehydration of this racemic diketone produces all-cis 3,4-dimethyl, 2,5-bis 3,4-dimethoxyphenyl)tetrahydrofuran which is hydrogenated at high pressure to produce the tetramethyl ether of N.D.G.A., this composition being further dealkylated to form the meso-product.

U.S. Pat. No. 3,769,350 to Perry discloses a method for synthesizing meso-N.D.G.A. from a protected ortho dihydroxybenzene. The claims of this patent are drawn to the synthesis of racemic 2,3-dimethyl-1, 4-bis(3,4-dialkoxyphenyl)1,4-butanedione, the starting material of the present process. This racemic composition is an intermediary in the process described in the patent for synthesizing meso-N.D.G.A.; however, unlike the present process, the patent discloses the conversion of this diketone intermediary to 3,4-dimethyl-2,5-bis(3,4-dialkoxyphenyl)-furan, and from thence through several routes to the final product. As in the above-described article, hydrogenation of the furan is conducted under pressure. Unlike the present invention, the process disclosed in the Perry patent and article does not produce optically active N.D.G.A., nor a racemic mixture thereof. Further, the Perry process requires the use of expensive and potentially dangerous high-pressure hydrogenation equipment which is not required to produce the isomer produced by the present invention.

U.S. Pat. No. 3,843,728, a division of the above Patent No. 3,769,350, discloses the same process and claims racemic 2,3-dimethyl,1,4-bis(3,4-dialkoxyphenyl) 1,4-butanedione compounds.

U.S. Pat. No. 3,906,004, also a division of the above Pat. No. 3,769,350, discloses the same process and claims the synthesis of meso-2,3-dimethyl-1,4-bis (3,4-dialkoxyphenyl)-butanedione from 3,4-dimethyl-2,5-bis(dialkoxyphenyl)-furan.

The d,1-form of the tetramethylether intermediate of d,1-N.D.G.A. (1,4-bis(3,4-dimethoxyphenyl)2,3-dimethyl butane) has been described by A.W. Schrecker, "Meso-Dihydroguaiaretic Acid and its Derivatives," *J. Amer. Chem. Soc.*, 79, 3823 (1957), along with an optically active isomer thereof.

Three d,1-diketone intermediates of the present process (1,4-bis(3,4-dimethoxyphenyl),2,3-dimethyl butanone, 2,3-bis(3,4-methylenedioxy benzoyl)butane, and 2-(4-benzyloxy-3-methoxybenzoyl),3-(3,4-methylenedioxy butane) have been described in T. Biftu, B. G. Hazra, R. Stevenson and J. R. Williams, *J. C. S. Perkin I*, 1147 (1978). The article describes the reduction of the racemic diketone by lithium aluminum hydride to a racemic diol. It also describes the direct hydrogenation of the d,1-diketone, using large amounts of palladium-carbon catalyst, to the d,1-tetramethyl ether.

In another article, T. Biftu, B. G. Hazra, and R. Stevenson, *J. C. S. Perkin I*, 2276 (1979), another d,1-diketone related to the diketone of the present process (1,4-bis(3,4,5-trimethoxyphenyl),2-3-dimethyl butane) is described. The diketone is reduced with lithium aluminum hydride to a racemic diol, which is hydrogenated with a palladium-carbon catalyst to the d,1-tetramethyl ether.

The use of a 48 percent solution of hydrogen bromide to dealkylate a solution of a des-methyl tetramethyl ether (1,4-bis(3,4-dimethoxyphenyl)-butane) in glacial acetic acid, to form des-methyl N.D.G.A. (1,4-bis(3,4-dihydroxyphenyl)butane) is described in O. Gisvold, D. Buelow, and E. H. Carlson, *J. Am. Pharm. Assoc.* 35, 188-91 (1946).

None of the foregoing prior art discloses the synthetic method of this invention, nor the optically-active isomers of N.D.G.A.

SUMMARY OF THE INVENTION

This invention is directed to the synthesis of compositions composed of optically active molecules of the formula:

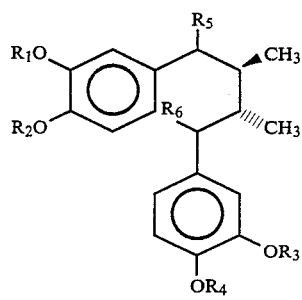

wherein $R_1$, $R_2$, $R_3$ and $R_4$ are independently H, lower alkyl, alkenyl, aryl, aralkyl, or aralkenyl groups, and/or $R_1$ and $R_2$ taken together, and/or $R_3$ and $R_4$ taken together, may form lower alkylene radicals; and, $R_5$ and $R_6$ are independently H, OH, O, lower alkoxy and lower aralkoxy groups. In the structural formulae given throughout this application, the substituents which are attached to the molecule above the plane of the molecule are designated by ▲ and those below the plane are designated by ⫽. Where no stereo-orientation is indicated, the substituents in the compound designated thereby can be either in their R or S orientation, and the compound can be a mixture of R and S isomers. Where the term "optical activity" is used herein it pertains only to bonds depicted by ▲ and/or ⫽. The optical orientation or assymmetry resulting from other bonds not so depicted is irrelevant. Unless otherwise specified, where only one optically active compound is depicted, its antipode, as well as racemic mixtures of both antipodes, are intended, it being understood that the orientation of these bonds is not altered throughout the process of this invention, so that the specific form of the starting material will determine the specific form of the intermediate compositions and final product.

A stereo-selective synthesis of d,1-nordihydroguaiaretic acid (d,1-2,3-dimethyl,1,4-bis(3,4-dihydroxyphenyl)butane) is provided in which the starting material is a diketone of optically active molecules of the formula:

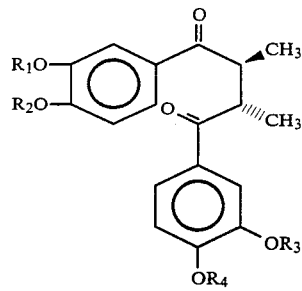

where $R_1$, $R_2$, $R_3$, and $R_4$ are as above described.

Formula I is reduced to form optically active molecules of a diol of the formula:

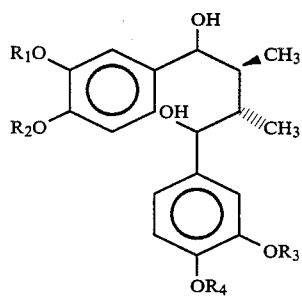

Formula II is alkylated to form optically active molecules of the formula:

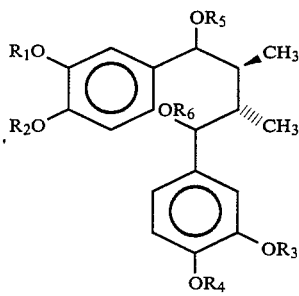

where $R_5$ and $R_6$ are independently lower alkyl, alkenyl, aryl, aralkyl or aralkenyl, or silyl, or substituted silyl with from one to three substituents which are, independently, lower alkyl, alkenyl, aryl, aralkyl or aralkenyl groups.

Formula III is then cleaved to form optically active molecules of the formula:

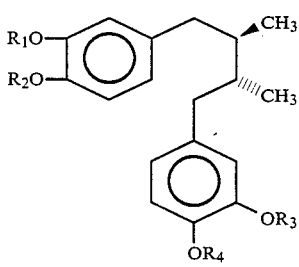

Compound IV is then dealkylated for form optically active molecules of N.D.G.A.:

V.

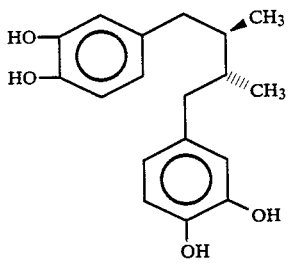

DETAILED DESCRIPTION OF THE PREFERRED EMBODIMENTS

As used throughout this application, the term "lower alkyl" refers to both straight and branched chain hydrocarbon groups containing from 1 to 6 carbon atoms, such as methyl, ethyl, propyl, etc., and the term "lower alkoxy" refers to the corresponding methoxy, ethoxy, etc. groups. The term "lower alkylene" includes both straight and branched chain alkylene radicals containing from 2 to 6 carbon atoms such as methylene, ethylene, propylene, butylene, isobutylene, etc. The term "lower aralkyl" or "lower aralkenyl" refers to aralkyl or aralkenyl groups containing 7 to 14 carbon atoms, such as phenyl lower alkyl, i.e., benzyl, phenylethyl, etc., and the term "lower aralkoxy" refers to the corresponding aralkoxy groups. The term "halogen" includes all four halogens, i.e., iodine, bromine, chlorine and fluorine.

In accordance with this invention, the starting material is a compound described by Formula I above obtained by means of syntheses known to the prior art, such as that described in U.S. Pat. No. 3,769,350.

In the specific embodiments described below, $R_1$–$R_6$ are methyl groups. Although it is understood that other substituents, as above defined, may also be used.

Molecules of optically active 1-4-bis(3,4-dimethoxyphenyl),2,3-dimethylbutane-1,4-dione (Formula I) are converted to molecules of optically active 1-4-bis(3,4-dimethoxyphenyl),2,3-dimethyl-butane-1,4-diol (Formula II) by reduction. Standard reducing agents such as sodium borohydride and lithium aluminum hydride may be used to carry out this reaction, and preferably the reducing agent is lithium aluminum hydride. The reaction is carried out in an inert organic solvent, preferably tetrahydrofuran, although any conventional solvent may be used, including water, methanol, ethanol or diethyl ether. The reaction may be carried out at a temperature of between about 0° C. and about 100° C., and preferably the materials are mixed at about 0° C. and slowly warmed to reflux temperatures. Product yields of between about 90 and about 100 weight percent are obtained. Critical to obtaining such yields are the maintenance of an excess of the reducing agent and neutral to basic conditions.

Optically active molecules of 1-4 bis(3,4-dimethoxyphenyl)2,3-dimethyl-butane-1,4-diol (Formula II) are then methylated to form optically active molecules of 1,4-bis(3,4-dimethoxyphenyl),2,3-dimethyl 1,4-dimethoxy-butane (Formula III). An alkali metal hydride, preferably sodium hydride, and a dry dialkyl formamide, preferably dimethylformamide, or other suitable sovlent such as tetrahydrofuran or dimethyl sulfoxide, are mixed with the diol, the hydride being added in excess amounts, namely at a molar ratio of reagent to starting compound of greater than about 2 and less than about 5. Methyl iodide (or other suitable alkyl halogen such as methyl bromide or ethyl iodide is then added to the mixture, also in excess, at a molar ratio of alkyl halogen to starting compound of greater than about 2 and less than about 5. The reaction is preferably carried out at ambient temperature, for a period of between about 0.5 and about 1 hour. Yields of between about 90 and about 100 weight percent are obtained when excess reagents over starting compounds are used, and the reaction is kept free of water and hydroxylic solvents.

Optically active molecules of 1,4-bis(3,4-dimethoxyphenyl), 2-3-dimethyl-1,4-dimethoxy-butane (Formula III) are then reacted to form 1,4-bis(3,4-dimethoxyphenyl), 2-3-dimethyl-butane (Formule IV) utilizing a mixture of sodium and ammonia in an inert organic solvent such as, preferably, tetrahydrofuran. Preferably, an excess of sodium is used, and the mixture is kept free of water or other hydroxylic solvents. Other reagents known to the art may be used to effect the cleavage, including lithium or potassium in lower alkyl amines; and other conventional inert organic solvents such as ethyl ether, and benzene may also be employed. The reaction is carried out at a temperature of between about −80° C. and about −33° C. The mixture is allowed to react for between about 10 and about 20 minutes, after which time the reaction should be stopped with a reagent such as ethanol or methanol. Allowing the reaction to go on for additional lengths of time results in reduction of the rings to a complex mixture. Yields of between about 90 and about 100 weight percent are obtained.

Optically active molecules of 1,4-bis(3,4-dimethoxyphenyl), 2,3-dimethyl-butane (Formula IV) are then converted to optically active molecules of nordihydroguaiaretic acid (1,4-bis(3,4-dihydroxyphenyl), 2,3-dimethyl-butane) (Formula V) by dealkylation. Preferably the dealkylation is carried out utilizing a halogen acid, preferably hydrobromic acid, in a solution of a concentration of about 48% plus or minus about 10 percent. The starting material and reagent, preferably at a mole ratio of greater than about 4, are heated in the absence of air, in a vacuum or inert atmosphere such as nitrogen or argon, to between about 100° C. and about 130° C. for at least about 8 to about 10 hours, and preferably about 9 hours. A yield of between about 90 and about 100 weight percent is obtained. Critical to obtaining such yields are the use of excess acid and the complete exclusion of oxygen.

Overall yield of d,1-nordihydroguaiaretic acid for the total synthesis beginning with the Formula I diketone is between about 45 and about 100 weight percent.

It is understood that the orientation of the carbon-methyl bonds in the 2,3-butane position remains unchanged throughout all the above reactions, and that the orientation of these bonds in the starting diketone determines the orientation of these bonds in the final product. Further, where the final product is a racemic mixture, the mixture may be separated into its antipodes by means known to the art.

The invention is further illustrated by the following examples:

EXAMPLES

EXAMPLE 1

1,4-BIS(3,4-DIMETHOXYPHENYL),2,3-DIMETHYL BUTANE-1,4-DIOL

To 1 g of lithium aluminum hydride suspended in 100 ml of tetrahydrofuran and cooled to ice temperatures under dry nitrogen was added 3.86 g of the starting diketone, 1,4-bis(3,4-dimethoxyphenyl),2,3-dimethyl butane-1,4-dione, in 30 ml of dry THF. The mixture was allowed to slowly come to room temperature while stirring and finally refluxed for 1 hour and then allowed to stand overnight. One ml of saturated sodium sulfate solution was added dropwise and stirring continued for several hours. Filtration and evaporation gave a colorless oil that crystallized on addition of ether. A yield of 3.93 g (quant.) was obtained. IR spectra showed no carbonyl.

EXAMPLE 2

1,4-BIS(3,4-DIMETHOXYPHENYL),2,3-DIMETHYL 1,4-DIMETHOXY BUTANE

To 3.9 g of starting diol in 20 ml of dried dimethyl formamide, stirring under nitrogen atmosphere, was added sodium hydride (washed repeatedly with dry hexane) in small portions until a large excess had been added. Methyl iodide was then added in excess and stirring continued for 1 hour. Water was added and the mixture was extracted with chloroform, the CHCl$_3$ evaporated and the residue run through a short silica gel column to remove DMF. Yield was 4.0 g (95% Theor.) of colorless goo that showed no carbonyl (DMF) in the IR spectra.

EXAMPLE 3

1,4-BIS(3,4-DIMETHOXYPHENYL),2,3-DIMETHYL-BUTANE

To approximately 100 mg of sodium, stirring in 200 ml of dry liquid NH$_3$ at $-80°$ C., was added 1.6 g of starting compound in 20 ml of dry THF. The blue color faded about halfway through the addition and another approximately 100 mg of sodium was added, followed by the remainder of the starting material. Additional sodium was added and the blue color maintained for 14 minutes at $-80°$ C. An additional 20 ml of dry THF was used to wash starting material from the syringe. Three ml of ethanol was added quickly to stop the reaction. The NH$_3$ and THF were evaporated under N$_2$. 100 ml of water was added and the product extracted into chloroform. Evaporation gave 1.4 g (Quant.) of colorless oil.

EXAMPLE 4

D-1 N.D.G.A.

To 100 mg of the starting tetramethyl ether in a heavy walled glass tube under nitrogen was added 1 ml of 48% hydrobromic acid. The tube was frozen in a liquid nitrogen bath and sealed in a vacuum. The tube was heated to 126° C. and stirred magnetically for 9 hours. After cooling overnight the tube was opened and water added and the solid product 82.6 mg (98% Theor.) filtered off. Gas chromatography mass spectrometry testing of the trimethyl silyl derivative showed this product to be about 95% Racemic N.D.G.A. with the major impurity being two isomers of a trimethyl product with methyl at the 1-butane position.

Although the foregoing invention has been described in some detail by way of illustration and example for purposes of clarity of understanding, it will be obvious that certain changes and modifications may be practiced within the scope of the invention, as limited only by the scope of the appended claims.

What is claimed is:

1. A composition of matter selected from the group consisting of optically active d,1-nordihydroguaiaretic acid isomers of the formula:

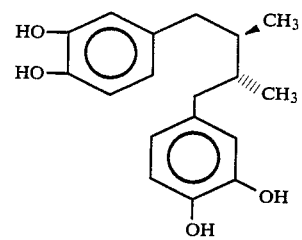

its antipode, and racemic mixtures thereof.

2. A composition of matter selected from the group consisting of d,1-isomers of the formula:

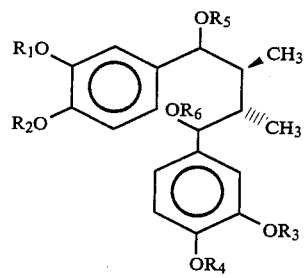

where
$R_1$, and $R_2$, are lower alkyl and aralkyl, and $R_3$, and $R_4$ are lower alkyl and aralkyl, and $R_5$ and $R_6$ are lower alkyl, alkenyl, aryl, aralkyl, or aralkenyl groups, or silyl, or substituted silyl with from one to three substituents which are lower alkyl, alkenyl, aryl, aralkyl or aralkenyl groups;
its antipode, and racemic mixtures thereof.

3. The composition of matter selected from the group consisting of optically active d,1-isomers of the formula:

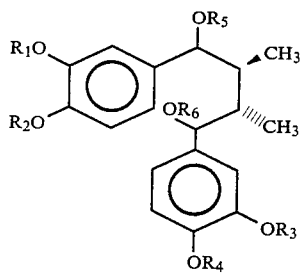

in which $R_1$, $R_2$, $R_3$, $R_4$, $R_5$ and $R_6$ are methyl.

* * * * *

UNITED STATES PATENT AND TRADEMARK OFFICE
CERTIFICATE OF CORRECTION

PATENT NO. : 4,562,298
DATED : Dec. 31, 1985
INVENTOR(S) : Robert M. Parkhurst and Ronald S. Pardini It is certified that error appears in the above—identified patent and that said Letters Patent is hereby corrected as shown below:

In column 3, line 41, insert --▼-- after the words "designated by . ."

In column 3, line 42, insert --≡-- after the words "designated by . ."

In column 3, line 50, insert --▼-- after the words "depicted by . ."

In column 3, line 50, insert --≡-- after the words "and/or . ."

In column 4, line 66, delete the word "for" and insert --to--.

Signed and Sealed this

Eleventh Day of March 1986

[SEAL]

Attest:

DONALD J. QUIGG

Attesting Officer

Commissioner of Patents and Trademarks